United States Patent [19]

Chanoch

[11] Patent Number: 5,308,341
[45] Date of Patent: May 3, 1994

[54] METHOD OF TESTING THE DOSE ACCURACY OF A MEDICATION DELIVERY DEVICE

[75] Inventor: Lawrence H. Chanoch, Mahwah, N.J.

[73] Assignee: Becton, Dickinson and Company, Franklin Lakes, N.J.

[21] Appl. No.: 127,850

[22] Filed: Sep. 28, 1993

[51] Int. Cl.⁵ ............................................. A61M 5/00
[52] U.S. Cl. .................................. 604/208; 604/207; 604/51
[58] Field of Search ................. 604/207, 208, 211, 51

[56] References Cited

U.S. PATENT DOCUMENTS

| | | | |
|---|---|---|---|
| 2,233,554 | 3/1941 | Pletcher | 604/208 |
| 2,648,334 | 8/1953 | Brown et al. | 604/208 |
| 4,498,904 | 2/1985 | Turner et al. | 604/211 |
| 4,936,833 | 6/1990 | Sams | 604/208 |
| 4,973,318 | 11/1990 | Holm et al. | 604/208 |
| 5,015,235 | 5/1991 | Crossman | 604/117 |
| 5,017,190 | 5/1991 | Simon et al. | 604/207 |

FOREIGN PATENT DOCUMENTS 2595947  9/1987  France ............... 604/208

*Primary Examiner*—John G. Weiss
*Attorney, Agent, or Firm*—John L. Voellmicke

[57] ABSTRACT

A method for testing the accuracy of a medication delivery device, such as a medication delivery pen, includes the steps of:

a) providing a syringe assembly having a hollow barrel with volume measuring indicia on the barrel, a slidable stopper in the barrel and a needle cannula at the distal end of the barrel;
b) providing a medication delivery pen having a pierceable septum at its distal end, a reservoir for containing liquid adjacent to the septum, a movable plunger for dispensing liquid from the reservoir projecting from the proximal end of the pen and dose setting apparatus for manually selecting the volume of liquid to be delivered by action of the plunger;
c) manually activating the dose setting apparatus to select the volume of liquid to be delivered from the pen;
d) piercing the septum of the pen with the needle cannula of the syringe;
e) activating the plunger to dispense the selected volume of liquid from the reservoir through the needle into the syringe barrel chamber so that as liquid enters the chamber the stopper is moved proximally along the syringe barrel chamber;
f) observing the volume of liquid dispensed into the syringe barrel chamber.

6 Claims, 4 Drawing Sheets

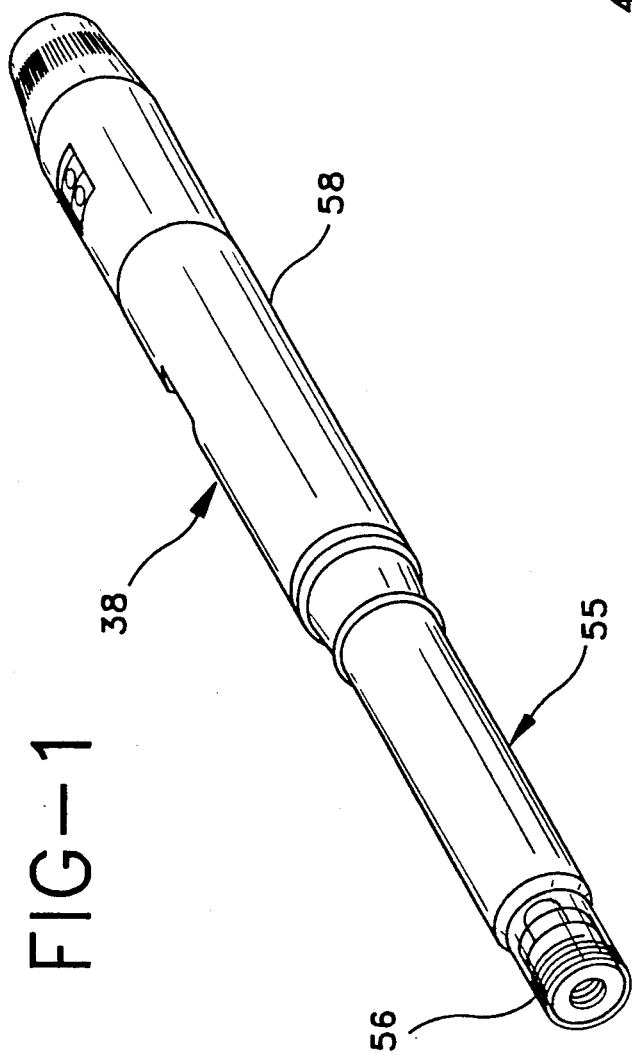
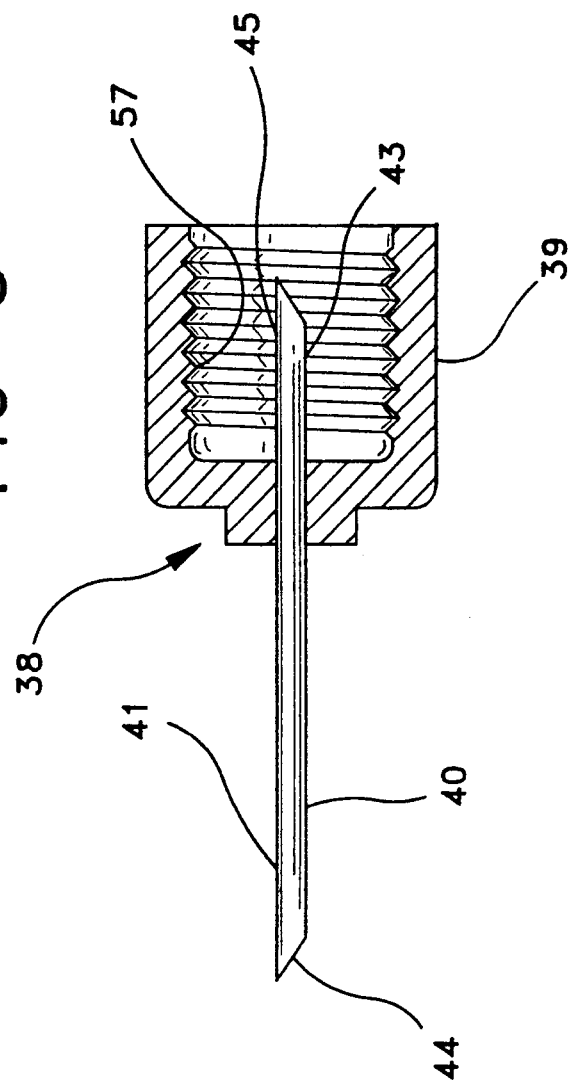

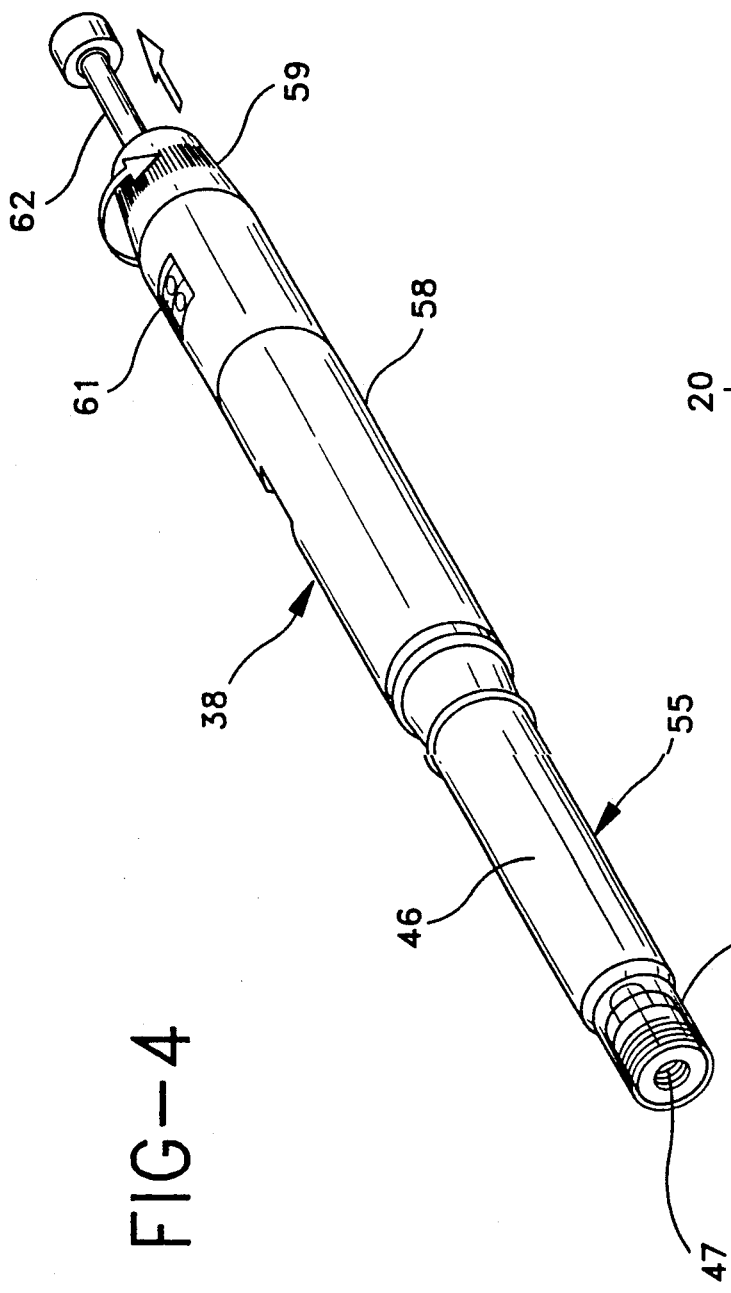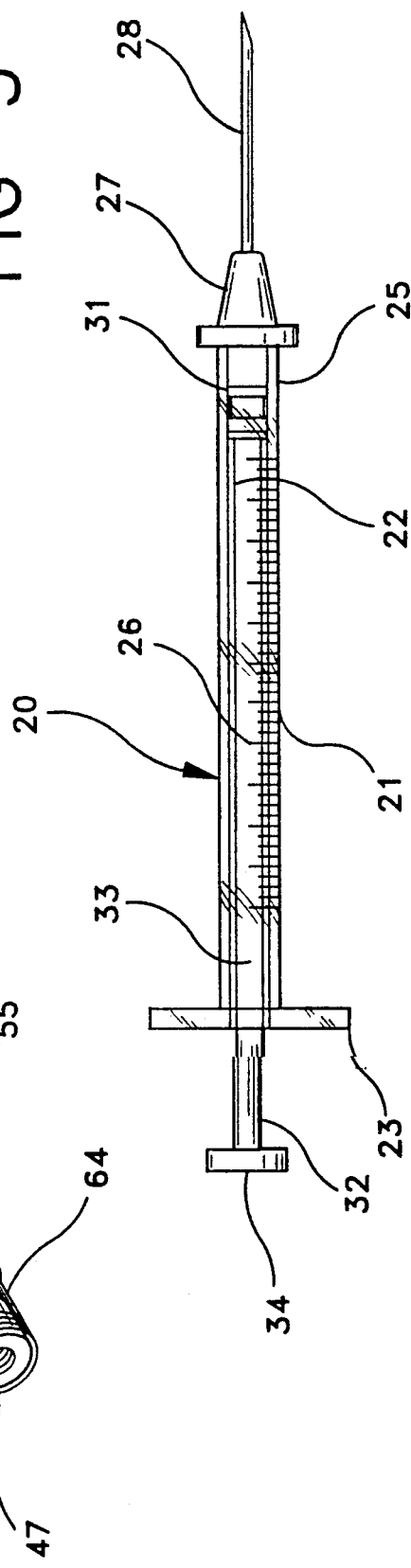

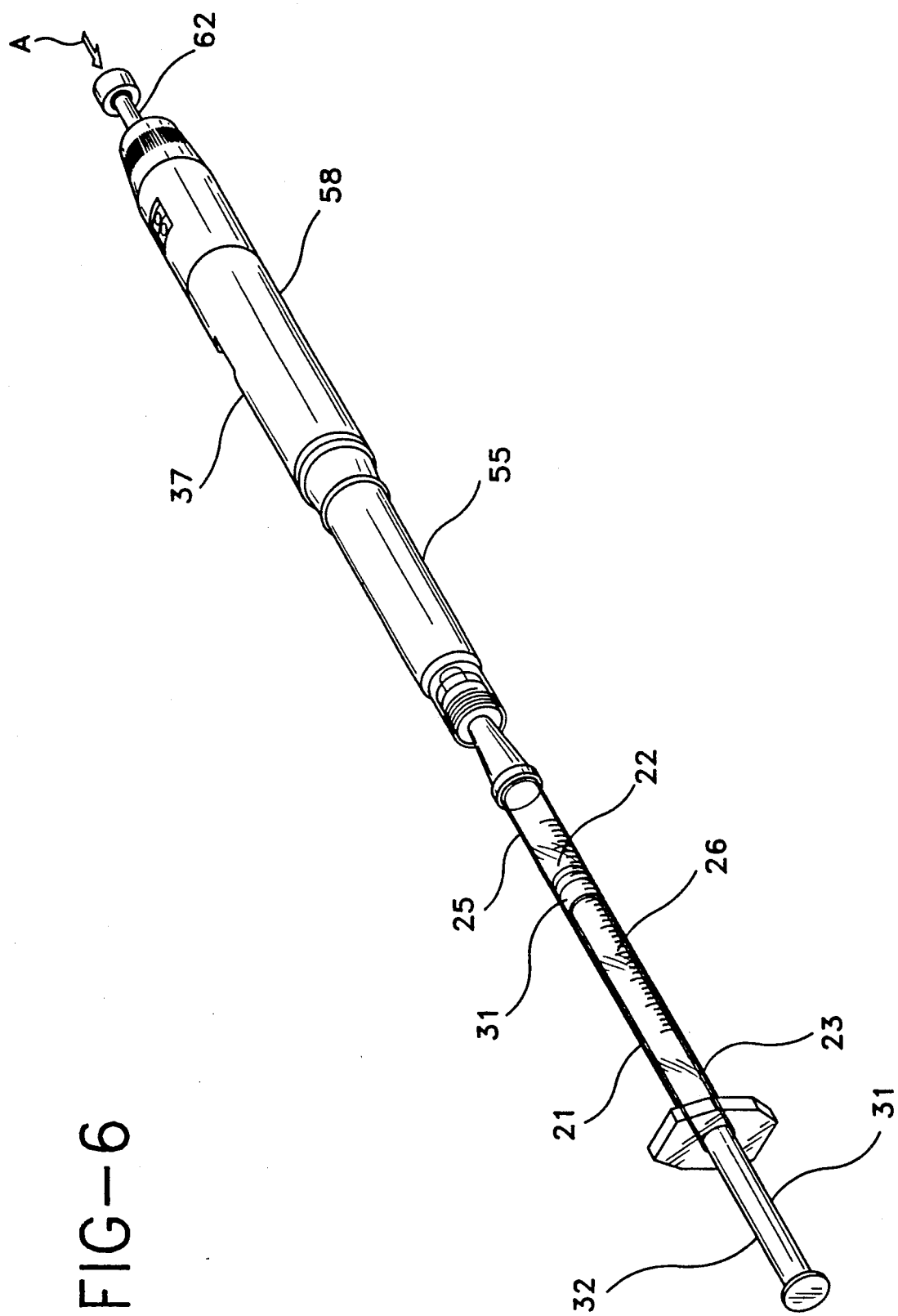

METHOD OF TESTING THE DOSE ACCURACY OF A MEDICATION DELIVERY DEVICE

FIELD OF THE INVENTION

The subject invention relates to medication delivery pens and a test method for determining the dose accuracy of medication delivery pens.

DESCRIPTION OF RELATED INFORMATION

Hypodermic syringes are used to deliver selected doses of medication to patients. Generally speaking, a hypodermic syringe includes a cylindrical syringe barrel having an open proximal end and a distal end. The barrel includes a cylindrical wall between the distal and proximal ends which defines a fluid receiving chamber. The proximal end of the barrel receives a stopper in fluid-tight engagement. A plunger rod extends proximally from the stopper out of the open proximal end of the barrel. The distal end of the barrel includes a passage communicating with the chamber. A needle cannula may be mounted to the distal end of the syringe barrel such that the lumen of the needle cannula communicates with the passage and the chamber of the syringe barrel. Movement of the plunger in a proximal direction draws fluid into the lumen of the needle cannula and into the chamber. Movement of the plunger in a distal direction urges fluid from the chamber and through the lumen of the needle cannula.

Medication to be injected with a prior art hypodermic syringe often is stored in a vial having a pierceable elastomeric septum. Medication in the vial is accessed by piercing the elastomeric septum with the needle cannula. A selected dose of medication may be drawn into the chamber of the syringe barrel by moving the plunger a selected distance in a proximal direction. The syringe barrel typically contains volume measuring indicia which allows the user to accurately measure the amount of liquid drawn into the barrel. The needle cannula may be withdrawn from the vial, and the medication may be injected into the patient by moving the plunger in a distal direction.

Some medication, such as insulin, is self-administered. The typical diabetes patient will require injections of insulin several times during the course of a day. The required dose of insulin will vary from patient to patient, and for each patient may vary during the course of the day and from day to day. Each diabetes patient will establish a regimen that is appropriate for his or her own medical condition and for his or her lifestyle. Each of these regimens may require the diabetes patient to periodically self-administer insulin in public locations, such as places of employment or restaurants. The required manipulation of the standard prior art hypodermic syringe and vial can be inconvenient and carrying vials and syringes can be embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a pen body which includes a driver and dose setting apparatus, as explained further below. A disposable medication containing vial for use with the prior art vial holder includes a distal end having a pierceable elastomeric septum that can be pierced by one end of a double-ended needle cannula. The proximal end of this vial includes a stopper slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivery by the pen and a driving apparatus for urging the stopper of the vial distally for a distance corresponding to the selected dose.

The user of the pen mounts a prior art double-ended needle cannula to the distal end of the vial holder such that the proximal point of the needle cannula pierces the septum on the vial. The patient then selects a dose and operates the pen to urge the stopper distally to deliver the selected dose. The dose selecting apparatus returns to zero upon injection of the selected dose. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above description describes a reusable medication delivery pen. Delivery pens may also be disposable. Disposable pens are discarded after the reservoir having the pierceable septum is emptied of its contents. In other respects their operation is similar to the description above.

A medication delivery pen such as an insulin pen provides many advantages to the active diabetic who must carry his medication delivery equipment with him throughout the day. The pen offers a self-contained mechanism for insulin administration. Insulin pens are well known in the art and are described in many patents. Most insulin pens use a double-ended needle having a threaded hub which engages the distal end of the pen and while simultaneously piercing the septum of the insulin reservoir.

The vast majority of all insulin is delivered through single-use plastic disposable syringes. Unlike the syringe, with the insulin pen it is not obvious if the correct dose has been injected, or if any insulin has been injected at all. The proper performance of insulin pens is critical to the well-being of the patient with diabetes. To date there is no known simple, accurate and economical method for a diabetic to verify the dose delivery of an insulin pen. One manufacturer provides a needle shield with a graduation line for a specific number of units of insulin. The user is instructed to inject the insulin through the needle into the cavity of the needle shield. A disadvantage of this method is that after the insulin is injected into the needle shield it must be thrown out. Insulin is expensive and providing an expensive test may discourage users from frequently checking their insulin delivery pens. Also, when the insulin delivered is more or less than the volume indicated by the line on the receptacle the user does not know how much more or how much less or if this amount is significant.

Accordingly, although the art teaches many medication delivery pens such as insulin delivery pens, both reusable and disposable, there still does not exist a simple, easy-to-use, economical method of testing the dosage accuracy of a medication delivery pen.

SUMMARY OF THE INVENTION

A method for testing the dose accuracy of a medication delivery device includes the steps of:

a) Providing a syringe assembly having a hollow barrel with volume measuring indicia on the barrel. The barrel includes an internal chamber, a stopper slidable in the chamber, and a needle cannula at the distal end of the barrel having a lumen therethrough in fluid communication with the chamber.

b) Providing a medication delivery pen of the type using a needle assembly having a hub and a needle held by the hub so that both ends of the needle protrude from the hub. The pen has a distal end including a pierceable septum and means for engaging the double-ended needle assembly so that one end of the needle pierces the septum. A reservoir is contained within the pen adjacent to the septum. A movable plunger for delivering liquid from the reservoir projects from the proximal end of the pen. Dose setting mechanism is provided for manually selecting the volume of liquid to be delivered by action of the plunger.

c) Manually activating the dose setting mechanism of the pen to select the volume of liquid to be delivered from the pen.

d) Piercing the septum of the pen with the needle cannula of the syringe so that the lumen of the needle cannula is in fluid communication with the reservoir of the pen.

e) Activating the plunger to dispense the selected volume of liquid from the reservoir through the lumen into the syringe barrel chamber so that as liquid enters the chamber the stopper is moved proximally along the chamber.

f) Observing the volume of liquid dispensed into the chamber.

After the accuracy of the medication delivery device is measured, the liquid in the syringe can be injected into a patient. Some syringes may come with their stoppers positioned at various distances from the distal end of the syringe. To perform this test most accurately, the stopper should be moved distally to attempt to eliminate any air volume in the graduated portion of the barrel.

BRIEF DESCRIPTION OF THE DRAWINGS

FIG. 1 is a perspective view representing a typical reusable medication delivery pen.

FIG. 3 is a cross-sectional view of the double-ended needle of FIG. 2 taken along line 3—3.

FIG. 4 is a perspective view of the medication delivery pen of FIG. 1 illustrating the dosage being set.

FIG. 5 is a side-elevation view of a typical disposable insulin syringe.

FIG. 6 is a perspective view showing the insulin syringe, with its needle piercing the pierceable septum at the distal end of the medication delivery pen, and a portion of the contents of the pen being delivered into the syringe barrel.

DETAILED DESCRIPTION

Figure 2:
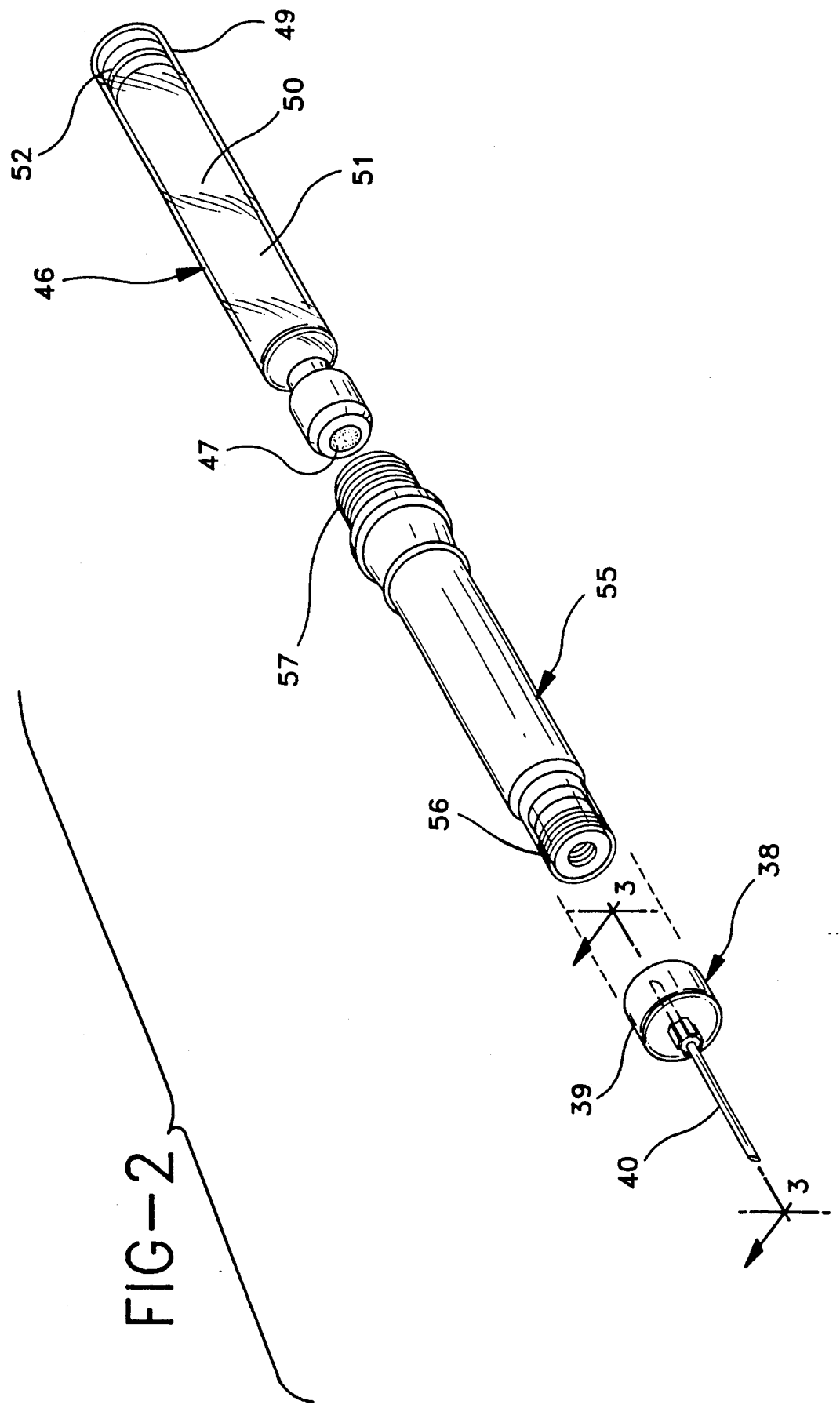
FIG. 2 is an exploded perspective view showing a medication vial having a pierceable septum at its distal end, a vial holder from the pen and a double-ended needle for use with the medication delivery pen.

While this invention is satisfied by many different steps and sequences, there is shown in the drawings and will herein be described a preferred method of the invention with the understanding that the present disclosure is to be considered exemplary of the principles of the invention is not intended to limit the invention to the specific method illustrated. The scope of the invention will be measured by the appended claims and their equivalents.

Adverting to FIGS. 1-6 a prior art hypodermic syringe assembly 20 includes an elongate hollow barrel 21 having a chamber 22 for retaining liquid. Barrel 21 includes open proximal end 23, distal end 25 and a tip 27 extending from the distal end and having a passageway therethrough in fluid communication with chamber 22. A needle cannula 28 extends distally outwardly from the tip and includes a lumen therethrough in fluid communication with the passageway.

For the purposes of the description of the present invention the term "distal end" is mean to refer to the end of the syringe closest to the needle and the end of the medication delivery pen closest to the pierceable septum while the term "proximal end" is mean to refer to the end of the syringe furthest from the needle and the end of the medication delivery pen from which the plunger extends.

Syringe 20 also includes an elastomeric stopper 31 slidably positioned in fluid-tight engagement inside barrel 21. The stopper is capable of moving fluid from chamber 22 through the passageway of the needle upon its movement toward distal end 25 of the barrel. The stopper is also capable of facilitating drawing fluid into the chamber through the passageway upon its movement away from distal end 25 of the barrel. A plunger rod 32 having an elongate body 33 engages stopper 31 to facilitate operation of the stopper. Body portion 33 extends outwardly from open proximal end 23 of the barrel. Disc-shaped plunger rod flange 34 is provided as a convenient structure for applying force to the plunger rod with respect to the barrel.

Some diabetics prefer to self-administer insulin using medication delivery pens such as medication delivery pen 37. Medication delivery pens are well known in the art and are taught in U.S. Pat. Nos. 4,498,904 and 4,973,318. Many medication delivery pens use a disposable needle assembly having a threaded hub and a double-ended needle cannula. Such a needle is discussed in U.S. Pat. No. 5,015,235 which teaches a needle package. As best illustrated in FIGS. 2 and 3, a prior art needle assembly 38 includes a cylindrically shaped hub 39 and needle cannula 40 having projecting distal end 41 and proximal end 43. Distal end 41 includes a sharpened tip 44 for injection of medication into the patient and, in this example, a sharpened tip 45 at proximal end 43 for piercing the septum of the pen liquid reservoir.

A typical reusable pen will use medication vials such as vial 46 having a pierceable septum 47 at its distal end. Vial 46 includes open proximal end 49 and interior cylindrical chamber 50 containing medication as illustrated by liquid 5 1. A resilient stopper 52 occludes pen proximal end 49 of the vial and is slidably movable within the vial and functions in the same manner as the syringe assembly stopper previously described. When all of the liquid in the vial is dispensed, the vial is thrown away and a new vial is used in its place.

Pen 37, in the illustrated pen, includes transparent removable vial holder 55 having a threaded distal end 56 adapted to engage internal threads 57 of needle hub 39. The transparent vial holder also includes a threaded proximal end 57 which screws into complementary threads in main body 58 of pen 37 to firmly hold and position the medication vial.

In use, a vial of liquid such as insulin is placed in the medication delivery pen and a disposable double-ended needle such as needle assembly 38 is attached to the distal end of the pen. As illustrated in FIG. 4, the user sets the dose by rotating dose selecting knob 59 of the pen until the numerical representation of the desired dose appears in window 61. Internal mechanism in the pen extends or allows the pen plunger 62 to extend proximally when the dose is set. The user then inserts the needle into the selected portion of his or her body and depresses plunger 62 until it travels its full stroke or as far as the pen will allow it to go. The needle may then be removed since the dose delivery is complete. In many pens the plunger will stay in the depressed position until the next dose is selected. Unlike the commonly used syringe, graduations on the medication delivery pen, if any, are not suitable for accurate dose measurement, so the user must accept, as a matter of faith, that the dose numerically represented in window 61 is the dose being delivered by depressing plunger rod 62. In cases such as with diabetics, the dose is critical to the therapy and providing more or less than the required dose can have serious consequences for the diabetic. Accordingly, it is important for the user, such as a diabetic, to check his or her pen from time to time to assure that an accurate dose of medication or other therapeutical liquid is being delivered.

A prior art method of determining dose involves supplying the double-ended needle and hub assembly in a rigid receptacle which has a volume indicating line printed on the receptacle. The diabetic will deliver a pre-determined dose of liquid, such as insulin, into the receptacle, such as 20 units. The line on the receptacle is designed to measure 20 units, exactly. The disadvantage of this method is that the insulin used for the test must be discarded and the expense of throwing insulin out may discourage users from using the test. In addition, if the insulin level is above or below the line, the user does not know the magnitude of the discrepancy and does not know if it is relevant or irrelevant.

The method of the present invention provides a simple, easy-to-use method for pen users such as diabetics for checking the dose delivered by their pen. The method of the instant invention also overcomes the shortcomings of known methods described hereinabove.

The preferred method of the present invention for testing the dose accuracy of pen 37 includes the following steps.

a) Provide a syringe assembly such as syringe 20 having a hollow barrel 21 with volume measuring indicia 26 along the barrel. The volume of liquid contained in the barrel is measured from the distal surface of stopper 31 using the volume measuring indicia. A typical diabetic syringe, such as a ½ cc insulin syringe for U-100 insulin, contains approximately 50 graduations so that the volume contained therein can be accurately measured. Further details of the syringe have been described hereinabove.

b) Providing a medication delivery pen, such as pen 37, of the type capable of using a double-ended needle assembly to deliver medication. Pen 37 includes a distal end 64 having a pierceable septum 47 and a reservoir containing liquid adjacent to the septum. Although this method can be practiced with reusable and disposable pens, the pen illustrated herein is reusable and uses a replaceable vial such as vial 46 of FIG. 2 to contain the liquid. Pen 37 further includes plunger 62 for delivering liquid from the reservoir. Plunger 62 projects proximally outwardly from the main body of the pen 58. The pen includes internal (not shown) dose-setting means for allowing the user to manually select the volume of liquid to be delivered. In the illustrated pen, dose selecting knob 59 is rotated until the numerical representation of the desired dose is visible through window 61.

c) Manually activating the dose selecting means to select the volume of liquid to be delivered from the pen.

d) As best illustrated in FIG. 6, piercing the septum of the pen with the needle cannula of the syringe so that the lumen of the syringe is in fluid communication with the reservoir of the pen.

e) Activating the plunger by applying manual force A to plunger 62 to dispense the selected volume of liquid from the reservoir of the pen through the lumen of the syringe needle into the syringe barrel chamber so that as the liquid enters the chamber, elastomeric stopper 31 moves proximally along elongate barrel 21.

f) Observing the liquid volume dispensed into barrel chamber 22 between the distal end of stopper 31 and the distal end of the barrel. The volume will be indicated by volume measuring indicia 26.

If the volume of liquid in syringe 20 is identical to the volume selected for delivery from pen 37 the user may now directly self-administer the liquid from the syringe to his or her own body. If the pen is delivering too much liquid the user may dispose of the additional liquid before injection. In addition, also, if the pen is delivering too little liquid the user may obtain additional liquid from another source to complete the medication regimen. It can be seen that the present method allows the user to determine not only if the exact dose set is being delivered but what the dose being delivered is in specific units. The user may then discard the pen if the delivered dosage is substantially different from the selected dose.

It can be seen that the order of the steps in the method of the present invention may be varied so long as the syringe and the pens are connected in the manner taught, and the pen is used to drive liquid from the pen reservoir into the chamber of the syringe.

Thus, the present invention provides a simple, easy-to-use method for determining the accuracy of a medication delivery pen such as an insulin delivery pen while not wasting the medication used for testing the volume delivery.

What is claimed is:

1. A method for testing the dose accuracy of a medication delivery device comprising the steps of:
   a) providing a syringe assembly having a hollow barrel with volume measuring indicia on said barrel, said barrel including an internal chamber, a slidable stopper in said chamber, a needle cannula at a distal end of said barrel, said needle cannula having a lumen therethrough in fluid communication with said chamber;
   b) providing a medication delivery pen having a distal end including a pierceable septum and means for engaging a needle assembly, a reservoir containing liquid adjacent to said septum, a movable plunger for delivering liquid from said reservoir, said plunger projecting from a proximal end of said pen, and dose setting means for manually selecting the volume of liquid to be delivered by action of said plunger;

c) manually activating said dose setting apparatus to select the volume of liquid to be delivered from said pen;

d) piercing the septum of said pen with said needle cannula of said syringe so that said lumen is in fluid communication with said reservoir;

e) activating said plunger to disperse the selected volume of liquid from said reservoir through said lumen into said syringe barrel chamber so that as liquid enters said chamber, said slidable stopper is moved proximally along said chamber; and f) observing the volume of liquid dispensed into said syringe barrel chamber.

2. The method of claim 1 further including the step of advancing said stopper to its distal-most position in said syringe barrel before said step of piercing said septum of said pen with said needle cannula of said syringe.

3. The method of claim 1 further including the step of disengaging said syringe from said pen before or after observing the volume of liquid delivered from said pen to said syringe barrel chamber.

4. The method of claim 1 wherein said liquid is liquid medication.

5. The method of claim 4 wherein said liquid medication is insulin.

6. The method of claim 3 further including the step of injecting all or part of said liquid into a person.

* * * * *